Figure 1:
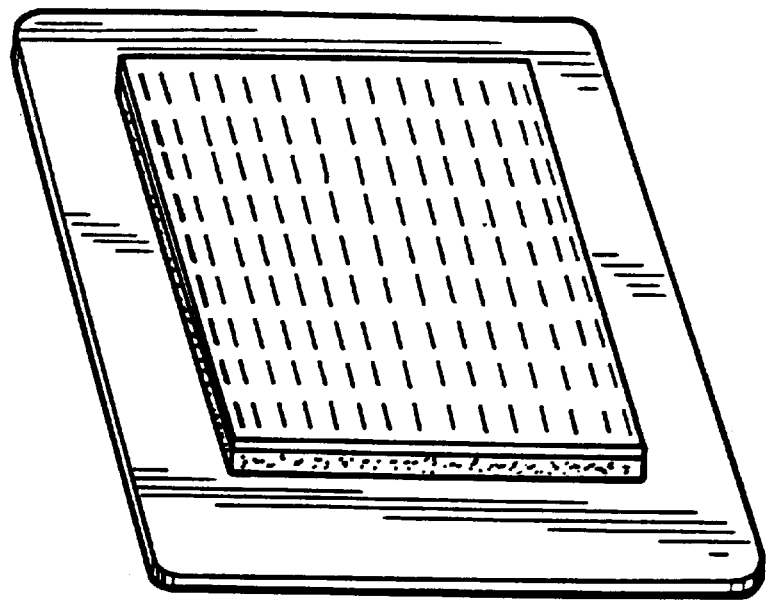

United States Patent [19]
Addison

[11] Patent Number: 5,981,822
[45] Date of Patent: Nov. 9, 1999

[54] ABSORBENT WOUND DRESSINGS

[75] Inventor: Deborah Addison, Via Lancaster, United Kingdom

[73] Assignee: Johnson & Johnson Medical, Inc., Arlington, Tex.

[21] Appl. No.: 09/067,866

[22] Filed: Apr. 28, 1998

[51] Int. Cl.[6] .................................................. A61F 5/00
[52] U.S. Cl. ........................... 602/41; 128/287; 602/56; 602/55
[58] Field of Search ................................ 602/41, 55, 56, 602/58; 128/287

[56] References Cited

U.S. PATENT DOCUMENTS

| | | |
|---|---|---|
| 2,877,765 | 3/1959 | Bunyan . |
| 3,399,672 | 9/1968 | Crowe et al . |
| 4,541,426 | 9/1985 | Webster . |
| 5,397,316 | 3/1995 | La Von et al. . |
| 5,584,801 | 12/1996 | Kuroyanagi et al. . |

FOREIGN PATENT DOCUMENTS

| | | |
|---|---|---|
| 0 122 085 | 3/1984 | European Pat. Off. . |
| 0 160 569 | 4/1985 | European Pat. Off. . |
| 821959 | 10/1956 | United Kingdom . |
| 2 175 208 | 5/1986 | United Kingdom . |

OTHER PUBLICATIONS

Japanese Patent Abstract Publication No. 07100197, Date of Filing Aug. 20, 1993. Title *Rolled Coating Material For Wound* (Copyright: ® 1995, JPO).

*Primary Examiner*—John G. Weiss
*Assistant Examiner*—Kelvin Hart
*Attorney, Agent, or Firm*—Andrew C. Farmer; Theodore Shatynski

[57] ABSTRACT

The invention provides a wound dressing (1) comprising a wound contacting sheet (4) laminated to one side of an absorbent layer (3) of water-swellable absorbent material such as a polyurethane. A liquid water-impermeable backing layer (2) is laminated to the other side of the absorbent layer (3). The wound contacting sheet is provided with one or more slits (5) therein. Expansion of the absorbent layer (3) due to absorption of wound exudate causes the slits (5) in the wound contacting sheet (4) to expand, thereby allowing passage of high flow rates of wound exudate. If the flow of exudate falls, then the slits close, thereby avoiding excessive drying of the wound surface.

11 Claims, 1 Drawing Sheet

ABSORBENT WOUND DRESSINGS

The present invention relates to absorbent wound dressings for application to exuding wounds.

It is customary to apply absorbent wound dressings to wounds in order to absorb wound exudate as it is produced, whilst protecting the wound from airborne contamination. A drawback of conventional absorbent wound dressings is that they frequently contain absorbent fibrous materials, such as cotton lint, that shed fibers into the wound causing irritation and inhibiting wound healing. A further drawback of some conventional absorbent wound dressings is that they can be too effective, resulting in excessive dryness at the surface of the wound.

EP-B-0091800 and EP-B-0123465 describe surgical dressings in which the wound contacting layer is a so-called "intelligent" polymer film. These polymer films are continuous sheets of polymer that have much higher moisture vapour permeability when wet than when dry. The films allow the passage of moisture vapour at high rates when the film is wet, but allow much less moisture vapour to pass through when the film is dry, thereby preventing excessive drying out of the wound surface. These dressings suffer from the drawback that, even when wet, the continuous intelligent films have fairly low moisture permeability. This can result in pooling of exudate under the film in heavily exuding wounds.

GB-A-2175208 describes wound dressings that have reservoir compartments filled with absorbent material. The compartments communicate with the surface of the wound through slits in a wound contacting layer. These dressings are of relatively complex construction, and are not responsive to differing rates of flow of wound exudate.

JP-A-07100197 describes wound dressings consisting of a layer of fibrous absorbent material laminated to a wound contacting film. Slits are provided in the wound contacting film and extend through the absorbent layer to allow the passage of wound exudate into the absorbent layer. The film is alleged to prevent the fibers of the absorbent layer from contacting the wound site. There is no suggestion that such dressings could be made responsive to differing rates of flow of wound exudate.

EP-A-0099748 describes wound dressings comprising an absorbent layer and a wound contacting net that functions to reduce the tendency of the dressing to adhere to the wound, and retains loose threads or particles that may be present in the core absorbent material. It is stated that the net should be sufficiently elastically extensible to adjust to any dimensional changes in the absorbent layer. However, there is no suggestion that the dressing is responsive to the rate of flow of wound exudate.

It is an object of the present invention to provide an improved absorbent wound dressing that can be applied to exuding wounds, and that is responsive to the rate of wound exudate production so that excessive dryness of the wound surface is avoided when there is little exudate being produced, but pooling of exudate under the dressing is also avoided when there is heavy exudate production.

The present invention provides a wound dressing comprising a wound contacting sheet laminated to one side of an absorbent layer of water-swellable absorbent material, characterized in that a liquid water-impermeable backing layer is laminated to the other side of the absorbent layer, and the wound contacting sheet is provided with one or more slits therein, whereby swelling of the absorbent layer due to adsorption of wound exudate causes the wound contacting sheet to bulge, thereby opening up the slits to increase the liquid permeability of the wound contacting sheet.

In use, the exudate passes through the slits in the wound contacting sheet and into the absorbent layer. The absorbent layer swells as it absorbs the exudate, and the swelling of the wound contacting layer causes the absorbent layer and the contacting sheet laminated thereto to bulge, thereby opening the slits in the contacting sheet wider and allowing the passage of high flow rates of exudate. As the wound dries out, the absorbent layer also dries out and shrinks, causing the slits in the wound contacting sheet to close up so that the flow rate of exudate through the contacting sheet is reduced and excessive drying out of the wound surface is avoided.

Preferably, a plurality of slits is provided in the wound contacting layer, and more preferably the plurality of slits are preferably substantially parallel.

Preferably, the wound contacting sheet is bonded to the layer of water-swellable absorbent material over at least part of its area, for example by adhesive or heat bonding. For example, a margin of the wound contacting sheet may be bonded to a margin of the absorbent layer. Preferably, the wound contacting sheet is bonded to the absorbent layer over substantially the whole wound contacting area of the dressing.

Preferably, the layer of water-swellable absorbent material is from 1.0 mm to 10 mm thick in the unswollen state. Preferably, the layer of water-swellable absorbent material expands by at least 25% in thickness when it is saturated with water. More preferably, it expands by at least 50% in thickness when it is saturated with water.

The water-swellable absorbent material may be any such material known for absorbing body fluids. Preferably, the water-swellable absorbent material comprises a water-swellable polymer, more preferably a polyurethane polymer such as the polyurethane foam that is commercially available from Johnson & Johnson Medical, Inc. under the Registered Trade Mark TIELLE.

The wound dressings according to the present invention further comprise a backing layer located on the side of the absorbent layer opposite to the wound contacting layer. The backing layer helps to confine the absorbent layer, to ensure that swelling of the absorbent layer results in bulging of the wound contacting layer to open the slits in the wound contacting sheet. The backing layer is substantially liquid-impermeable to prevent leakage of wound exudate from the absorbent layer into clothes, bedclothes etc. For example, the backing layer may be formed from water vapour and gas-permeable, water and microbe-impermeable polyurethane film of the kind conventionally used for adhesive wound dressings. The backing layer is preferably bonded to the absorbent layer by heat or adhesive. Preferably, a layer of medical grade pressure-sensitive adhesive extends over the whole inner surface of the backing layer to bond the backing layer to the water-swellable absorbent layer. The adhesive also modifies the air- and water-permeability of the backing layer to give it the desired characteristics.

Preferably, the backing layer extends beyond the edges of the absorbent layer and of the wound contacting sheet to form a margin around the absorbent layer and the wound contacting sheet, and adhesive is provided on the margin for securing the margin of the backing layer to the skin of the patient around a wound. The same layer of adhesive preferably extends over the whole inner surface of the backing layer, for the reasons given above.

It will be appreciated that the use of the term "wound contacting sheet" here and elsewhere in the specification, does not exclude the possibility that dressings according to the present invention may have a further layer between the wound contacting sheet as herein defined and the wound surface. For example, there may be a further layer of gel, or a wound contacting hydrogel net to assist removal of the wound dressing from the wound surface and provide a more wound-friendly contacting surface.

It is envisaged that the wound dressings according to the present invention will be packaged in conventional fashion in sterile packaging, and sterilized in conventional fashion, such as by gamma-irradiation.

Figure 2:
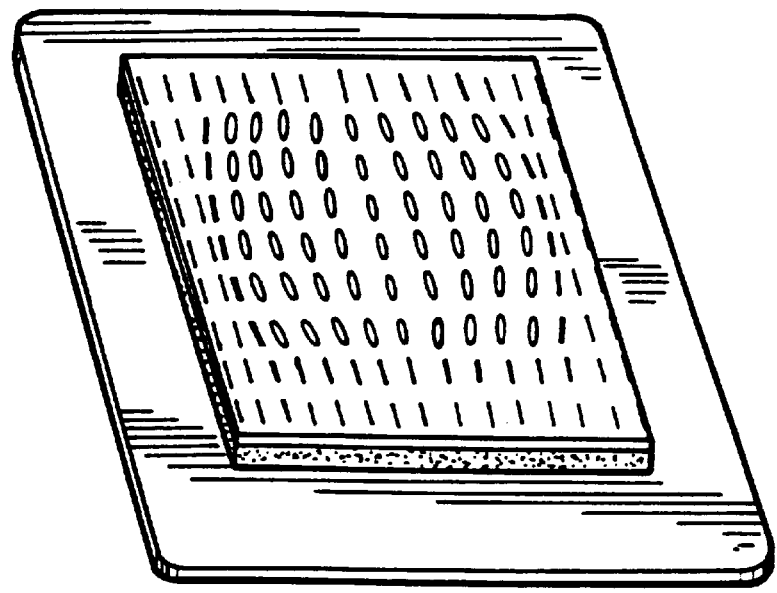

Specific embodiments of the wound dressing according to the present invention will now be described further, by way of example, with reference to the accompanying drawings, in which:

FIG. 1 shows a perspective view of a wound dressing according to the present invention immediately before application to an exuding wound; and FIG. 2 shows the wound dressing of FIG. 1 following application to an exuding wound, showing the effect of exudate absorption and swelling on the structure of the wound dressing.

Referring to FIG. 1, the wound dressing comprises a backing layer 2 formed from a water-repellent or water-impermeable elastomer. A particularly suitable material is Medifix 4005 (Registered Trade Mark) supplied by the Medifix company which is a polyurethane foam of blocked toluene diisocyanate nature, and is predominately closed cell.

The wound dressing further comprises an absorbent layer 3 approximately 1.5 mm thick of a water-swellable polyurethane formed from a prepolymer. The prepolymer is preferably an isocyanate-capped polyether, such as ethyleneoxy/propylenoxy copolymer. A particularly suitable prepolymer is available under the Registered Trade Mark HYPOL supplied by Hampshire Chemicals.

The wound dressing further comprises wound contacting sheet 4 having a plurality of linear, parallel slits 5 therein. The sheet 4 is bonded to the surface of the absorbent layer either by a layer of medical grade adhesive or by a suitable heat laminating process. The wound contacting sheet is formed from a medical grade elastomer. A particularly suitable material is a polyurethane film. The slits are preferably die-cut, and are preferably 2 mm to 20 mm long.

The backing layer 2 extends beyond the edges of the absorbent layer 3 and wound contacting sheet 4 to form a circumferential margin 6 approximately 1 cm wide, which is coated with a layer of pressure-sensitive adhesive of the kind conventionally used in the wound dressing art. Prior to use, the adhesive is protected by release-coated paper sheets (not shown) in conventional fashion.

In use, the dressing 1 is applied to an exuding wound. The wound exudate flows through the wound contacting sheet 4 into the absorbent layer 3, where it is trapped and causes the polyurethane polymer to swell. This results in the situation shown in FIG. 2, where it can be seen that swelling of the absorbent layer has caused the wound contacting sheet 4 to bulge outwardly, opening the slits 5 to ovoid shapes that allow passage of high flow rates of exudate into the absorbent layer. This process is, of course, reversible when the rate of exudate production falls, causing the absorbent layer to dry out due to evaporation of water vapour through the semi-permeable backing sheet 2.

It can thus be seen that this absorbent wound dressing can handle a wide range of exudate flow rates, avoids shedding of absorbent material into the wound bed, and prevents excessive drying out of the wound surface.

The above embodiment has been described by way of example only. Many other embodiments falling within the scope of the accompanying claims will be apparent to the skilled reader.

I claim:

1. A wound dressing comprising a wound contacting sheet laminated to one side of an absorbent layer of reversibly water-swellable absorbent material, characterized in that a liquid water-impermeable backing layer is laminated to the other side of the absorbent layer, and the wound contacting sheet is provided with one or more slits therein, whereby swelling of the absorbent layer due to absorption of wound exudate causes the wound contacting sheet to bulge, thereby opening up the slits to increase the liquid permeability of the wound contacting sheet.

2. A wound dressing according to claim 1, wherein a plurality of said slits are provided in the wound contacting sheet.

3. A wound dressing according to claim 2, wherein said plurality of slits are substantially linear and parallel.

4. A wound dressing according to any preceding claim, wherein the wound contacting sheet is bonded to the layer of water-swellable absorbent material over at least part of its area.

5. A wound dressing accordingly to claim 4, wherein the wound contacting sheet is bonded to the layer of water-swellable absorbent material over substantially the whole wound contacting area of the dressing.

6. A wound dressing according to claim 1, wherein the layer of water-swellable absorbent material is from 1.0 mm to 10 mm thick in the unswollen state.

7. A wound dressing according to claim 1, wherein the water-swellable absorbent material comprises a water-swellable polymer.

8. A wound dressing according to claim 7, wherein the water-swellable polymer comprises a polyurethane.

9. A wound dressing according to claim 1, further comprising a liquid-impermeable backing layer on the side of the absorbent layer opposite to the wound contacting layer.

10. A wound dressing according to claim 1, wherein the backing layer extends beyond the absorbent layer and the wound contacting sheet to form a margin around the absorbent layer and the wound contacting sheet, and adhesive is provided on said margin for securing said margin to the skin of a patient around a wound.

11. A wound dressing according to claim 8, which is sterile packaged.

* * * * *